United States Patent [19]

Sarngadharan et al.

[11] Patent Number: 5,116,740
[45] Date of Patent: May 26, 1992

[54] METHOD FOR PRODUCING NATIVE HIV GP160

[75] Inventors: Mangalasseril G. Sarngadharan, McLean, Va.; Vaniambadi S. Kalyanaraman, Germantown, Md.

[73] Assignee: Akzo N.V., Arnhem, Netherlands

[21] Appl. No.: 362,548

[22] Filed: Jun. 7, 1989

Related U.S. Application Data

[63] Continuation of Ser. No. 232,859, Aug. 16, 1988, abandoned.

[51] Int. Cl.$^5$ .............................................. C12N 7/00
[52] U.S. Cl. .................................. 435/70.4; 435/236; 435/5; 435/974
[58] Field of Search .................. 435/70.4, 236, 5, 974; 530/395, 826

[56] References Cited

PUBLICATIONS

Kalyanaraman et al, Aids Research and Human Retroviruses 4:319-329 (88).
Getchell et al, J. Clinical Microbiology 23:737-741 (86).
Pyle et al, J. of Virology 62:2258-2264 (88).

*Primary Examiner*—Douglas W. Robinson
*Assistant Examiner*—Sandra E. Saucier
*Attorney, Agent, or Firm*—William M. Blackstone

[57] ABSTRACT

Human Immunodeficiency Virus (HIV) glycoprotein gp160 is produced in its native form using a clone of HUT78 cells chronically infected with HTLV-III$_{451}$, and grown in serum-free medium.

2 Claims, 4 Drawing Sheets

① Glycoproteins eluted from Lentil-lectin Sepharose
② HTLV-III$_{451}$ gp160 from anti HIV-I gp41 Sepharose
③ Standard proteins

METHOD FOR PRODUCING NATIVE HIV GP160

The invention described herein was made during the course of work performed under National Cancer Institute, Department of Health and Human Services Contract No. NO1-CP-67694.

This is a continuation of Ser. No. 232,859, filed Aug. 16, 1988, now abandoned.

BACKGROUND OF THE INVENTION

The present invention relates to the production of native gp160 of human immunodeficiency virus (HIV), the etiologic agent of Acquired Immune Deficiency Syndrome (AIDS).

Human Immunodeficiency Virus (HIV) is now well established as the etiological agent of acquired immunodeficiency syndrome (AIDS). The virus is tropic for cells bearing the CD4 antigen and is highly cytopathic for helper-inducer (T4) cells. The envelope gene product of HIV is synthesized as a gp160 precursor molecule, which is subsequently processed into the external envelope protein gp120 and the transmembrane protein gp41. The precursor/product relationship between gp160 and the smaller proteins, gp120 and gp41, has now been well documented, as well as the amino acid sequences of all three [Allan, et al., Science, 228:1091-1094 (1985) and Veronese, et al, Science, 229:1402-1405 (1985)]. The external glycoprotein gp120 binds to the CD4 molecule on susceptible cells in the initial phase of viral cell fusion and giant cell formation induced by the virus [Dalgleish, et al., Nature, 312:763-766].

In addition to their role in cell surface receptor recognition and cell fusion, HIV gp120 and gp41 are the primary targets for immune recognition in individuals infected with HIV. Hence, these proteins have received special attention in virus neutralization studies and vaccine development. It has been observed that large segments of gp120 expressed by recombinant DNA techniques, or native gp120 purified from HIV-infected cells, elicit mostly type-specific neutralizing antibodies in animals. In addition, the HIV envelope precursor protein gp160 expressed in insect cells with baculovirus vectors produced a strong type-specific immune response in goats [Rusche, et al., PNAS, USA 84:6924-6928 (1987)].

The ability to infect certain cell lines with HIV, and to establish the infected cells into a continuous producer of intact virus has been described in U.S. Pat. No. 4,652,599. Even the ability to infect the cell line and the HIV variant of the present invention have been previously described [Getchell, et al., J. Clin. Microbiol. 23:737-742 (1986)].

However, neither of these events alone permitted the establishment of a process capable of producing the HIV glycoprotein gp160 in its native form. Normally, native gp160 breaks down into gp120 and gp41. Consequently, the envelope protein obtained from cell culture media or from lysed virus is gp120 and gp41. It is therefore most surprising that gp160 may be obtained in its native form.

Glycoprotein gp160 has only been produced through recombinant means. However, recombinant gp160 is different than the native gp160, particularly in regard to glycosylation. These differences become critical in the search for an HIV vaccine, particularly since the envelope glycoproteins of HIV determine viral tropism and harbor epitopes which are essential for the development of neutralizing antibodies against the virus.

SUMMARY OF THE INVENTION

It is an object of the present invention to provide a unique clone of HUT78 cells which, when chronically infected with HTLV-III$_{451}$, releases functionally intact viral glycoprotein gp160 into the extracellular medium.

Another object of the present invention is to provide an immortalized cell line grown in a serum-free medium under such conditions that the cell line releases gp160 in its native form into the medium.

Yet another object of the present invention is to provide intact HIV gp160 in its native form.

These and other objects and advantages of the invention are accomplished by growing infected cell line 6D5$_{451}$ in a serum-free medium, and isolating the native gp160 released by the cells into the medium.

DESCRIPTION OF THE FIGURES

FIG. 2 shows the release of HIV-specific proteins by 6D5$_{451}$ cells.

FIG. 3 shows the inhibition of HIV-induced syncytium formation by HTLV-III$_{451}$ glyocoproteins. CEM cells were cocultivated with Molt-3/HTLV-III$_B$ cells as described below. The cells were photographed after 48 hours. To study the effects of the viral glycoproteins, CEM cells were pre-incubated for 1 hour with the proteins before cocultivation.

DESCRIPTION OF THE PREFERRED EMBODIMENTS

A single cell clone of HUT78 cells has been infected with Human Immunodeficiency Virus Type 1 (HIV-1), whereby the infected cell line became a continuous producer of virus. Clone 6D5 is susceptible to chronic infection with HIV-1, as described in Getchell, et al., J. Clin. Microbiol., 23:737-742 (1986). Clone 6D5 is infected with a specific strain of HIV-1, HTLV-III$_{451}$, to produce the infected cell line 6D5$_{451}$. The infected cell line is then grown in serum-free medium, by pelleting 6D5$_{451}$ cells and resuspending them in serum-free medium (such as HB101 medium, commercially available from Du Pont). Serum-free medium HB104, also available from Du Pont, may also be used in the practice of this invention.

Only when serum-free medium is used can glycoprotein gp160 be separated from other proteins in the media. gp160 cannot be excluded from other media components when serum-containing media is used.

In the preferred embodiment, the HB101 medium also contains growth supplements such as transferrin, insulin, and bovine serum albumin. To assist in the growth of cells, the cells were subcultured every four days. The 6D5$_{451}$ cells were grown for 2 to 3 generations. The amount of HIV proteins released into the media, as measured by extracellular reverse transcriptase activity, was nearly five-fold greater in serum-free medium than in serum-containing medium. Reverse transcriptase (RT) in the culture medium of the infected cells was analyzed with $(dT)\sim_{15}\cdot(A)_n$ as primer template, as described in Poiesz, et al., *PNAS, USA*, 77:7415–7419 (1980).

Figure 1:
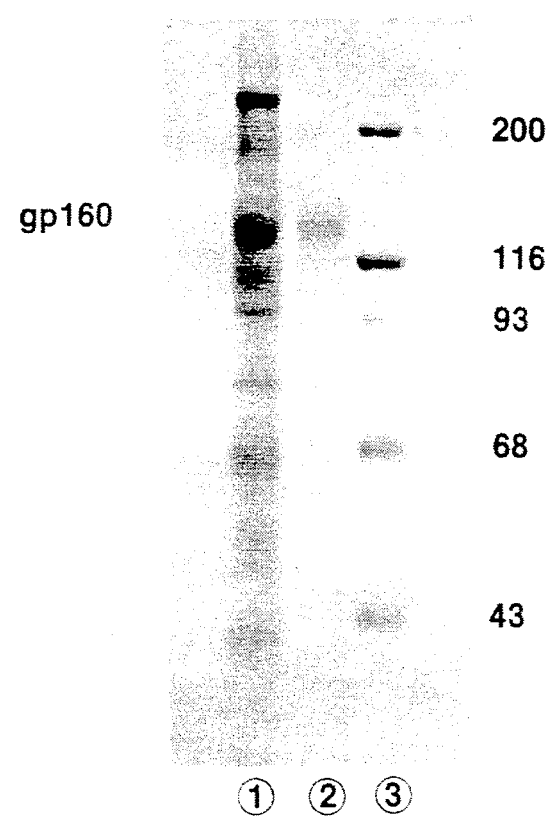
FIG. 1 (lane 1) shows the SDS-PAGE profile of the glycoprotein eluted from the lentil lectin Sepharose. Lane 2 shows the purified gp160 stained with Coomassie blue.

The cell-free medium was used as the source of the glycoprotein. The medium was adjusted to 20 mM with sodium phosphate, pH 7.5, 0.5% Triton X-100, 0.1 mM phenylmethylsulfonyl fluoride, and 400 mM sodium chloride. After incubation at room temperature for one hour, the medium was concentrated 30-fold with a Pellicon cassette system, commercially available from Millipore. Extraneous proteins derived from the media supplement were removed from the concentrate by immunoaffinity absorption (overnight) with a Sepharose-bound goat antibody raised against the proteins in the growth supplement in the serum-free medium. Proteins which bound to the goat antibody were removed, and the unbound material was then passed through a lectin affinity column, preferably a lectin-Sepharose column (Pharmacia). Although the use of a lentil lectin column is preferred, other lectins which will recognize mannose, such as concanavalin-A, may also be employed. After washing with phosphate buffered saline (PBS), the column was eluted with 400 mM alpha-methylmannoside in order to recover the viral glycoprotein. Although the use of methylmannoside to elute the column is preferred, any mannose, pyranoside, or saccharide which competes with the lectin in the affinity column may be used. FIG. 1 (lane 1) shows the SDS-PAGE profile of the glycoprotein eluted from the lentil lectin-Sepharose. The prominent glycoproteins in the samples were the 120 and 160 kD proteins. These proteins also reacted strongly in immunoblots with HIV-1 antibody-positive human serum. The immunoblot analysis of HTLv-III451 glycoprotein is carried out by a well known procedure, such as described in Sarngadharan, et al., *Science* 224:506–508 (1984). Essentially, the proteins are run on 7% SDS-polyacrylamide gels and transferred to nitrocellulose strips (commercially available). The nitrocellulose strips are then treated with the appropriate antibodies, and the blots are developed with peroxidase-conjugated secondary antibodies; the bands are visualized by reacting the strips with diaminobenzidine.

gp160 was purified from the mixture of glycoproteins eluted from lentil-lectin Sepharose column by immunoaffinity chromatography using a monoclonal antibody to HIV-1 gp41 protein. The monoclonal antibody was developed using partially purified HTLV-III$_{451}$ glycoproteins by standard techniques. The immunoglobulin fraction of the antibody was coupled to Sepharose according to the method described by the manufacturer (Pharmacia). The eluate from the lentil-lectin Sepharose column was equilibrated at 4° C. with the anti-HIV-1 gp41 Sepharose in 20 mM Tris-HCl, pH 8.5 containing 0.5% Triton X-100, 1M potassium chloride, and 0.1 mM PMSF. The Sepharose was then packed in a column, washed with PBS and the bound protein was eluted with 100 mM sodium bicarbonate. The HTLV-III$_{451}$ gp160 eluted from the column in a nearly homogenous state. FIG. 1 (lane 2) shows the purified gp160, separated by SDS-PAGE and stained with Coomassie blue.

Glycoprotein gp160 and its derivatives, prepared according to the present invention, may be employed in a conventional manner in immunotherapeutic and/or immunodiagnostic methods and compositions. Such methods of treatment and quantities employed are well-recognized in the art, and may be chosen by those of skill in the art from available methods and techniques. For example, gp160, as produced in accordance with the present invention, may be combined with a pharmaceutically acceptable adjuvant in an amount effective to provide diagnostic utility in an ELISA assay.

A deposit of the 6D5$_{451}$ strain described herein was made under the requirements of the Budapest Treaty with the American Type Culture Collection (ATCC), 12301 Parklawn Drive, Rockville, Md. 20852, USA, on Jan. 9, 1989.

Although the above description of the invention includes a recitation of preferred embodiments, this is not intended to limit the invention.

In order that the invention herein described may be more fully understood, the following Examples are set forth. It should be understood that these examples are for illustrative purposes only, and are not to be construed as limiting the invention in any manner.

EXAMPLES

Example 1

Figures 2A, 2B:
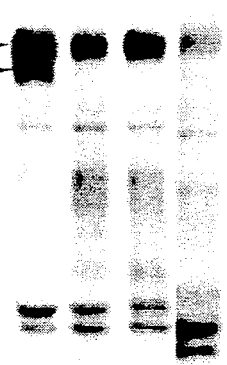
FIG. 2A: medium from cells grown in FCS.
FIG. 2B: medium from cells grown in HB101. Lane 1: HIV-positive human serum; Lane 2: rabbit anti-HTLV-III$_B$ gp41; Lane 3: rabbit anti-121 peptide (Centocore); Lane 4: goat anti-HTLV-III$_B$ gp120; Lane 5: normal human serum; Lane 6 normal rabbit serum; Lane 7: normal goat serum.

Twenty million 6D5$_{451}$ cells were labeled for 15 hours in 10 ml of the HB101 serum-free medium, containing 5% of the normal amount of methionine, 1 mCi of $^{35}$S-methionine, and 5% dialyzed HB101 supplement. The cell-free supernatant was filtered through a 0.45 micron filter, concentrated, and treated with 0.5% Triton X-100, 500 mM sodium chloride, and 1 mM phenylmethylsulfonyl fluoride. After one hour at room temperature, the solubilized medium was mixed with an equal volume of PBS containing 0.5% Triton X-100, 1% deoxycholate, and 0.1% sodium dodecyl sulfate (PBS-TDS). One milliliter of the mixture was incubated overnight with 10 ul of an anti-HIV serum and 150 ul of 10% protein-A Sepharose. The Sepaharose was pelleted, washed four times with PBS-TDS and boiled for 2 minutes with 1% SDS, 1% beta-mercaptoethanol, and 125 mM Tris-HCl (pH 6.8). The solubilized labeled proteins were separated on 7.5% SDS polyacrylamide gel and autoradiograghed as described in Veronese, et al., *Science* 229:1402–1405 (1985). FIG. 2 shows gp160 as a distinct immunoreactive protein product in the culture medium.

Example 2

The viral proteins in the extracellular medium of 6D5$_{451}$ cells grown in serum-free medium were analyzed by metabolic labeling with $^{35}$S-methionine, as described above. The released radioactive proteins were immunoprecipitated with either HIV-1 seropositive human serum or antibodies specific to HTLV-III$_B$ gp120 or gp41. HIV-1 positive human serum precipitated, in addition to the major core protein (p24), two proteins of approximately 120 kD and 160 kD. A goat antibody to HTLV-III$_B$ gp120 precipitated both the 120 kD and the 160 kD proteins, suggesting that they contain immunoreactive domains of gp120. On the other hand, rabbit anti-gp41 immunoprecipitated only the 160 kD protein. These results indicate that the 160 kD protein has both gp120 and gp41 domains of HIV, while the 120 kD protein has only the gp120 epitopes of HIV.

Example 3

The native 120 and 160 kD glycoproteins produced in accordance with this invention were further characterized by their reactivities with antibodies specific for HTLV-III$_B$ gp120 and gp41. For this purpose, the proteins were separated by SDS-PAGE, transferred to nitrocellulose strips, and treated with antibodies specific to HTLV-III$_B$ gp120 and gp41. Both the 120 and 160 kD proteins reacted with the HIV-1 positive serum, and with the goat anti-gp120. Only the gp160 kD protein reacted with the antibodies to HTLV-III$_B$ gp41. Of the two monoclonal antibodies to gp120 used, only one reacted with both, showing type-specific reactivities of the monoclonal antibodies with different isolates of HIV.

Example 4

Figure 3A:
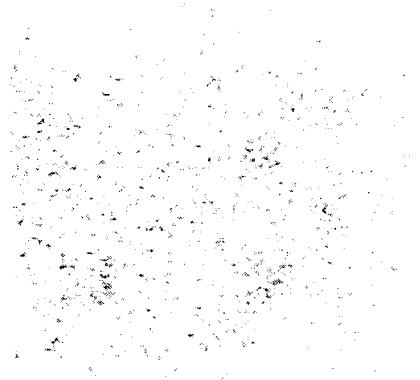
FIG. 3A: untreated CEM cells.
Figure 3B:
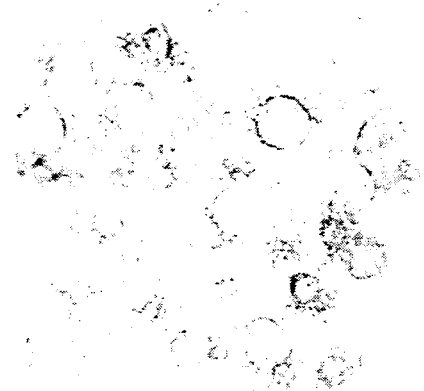
FIG. 3B: CEM cells plus Molt-3/HTLV-III$_B$ cells.
Figure 3C:
FIG. 3C: CEM cells pretreated with glycoproteins from uninfected 6D5 cell culture.
Figure 3D:
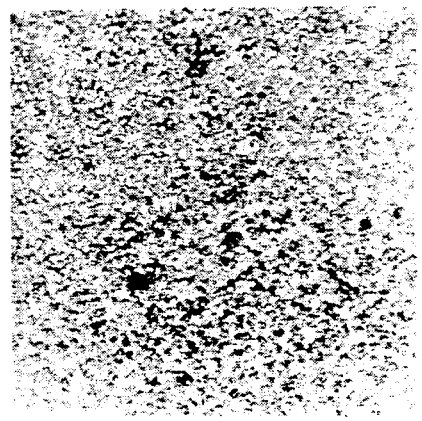
FIG. 3D: CEM cells pretreated with 6D5$_{451}$ glycoproteins.
Figure 4:
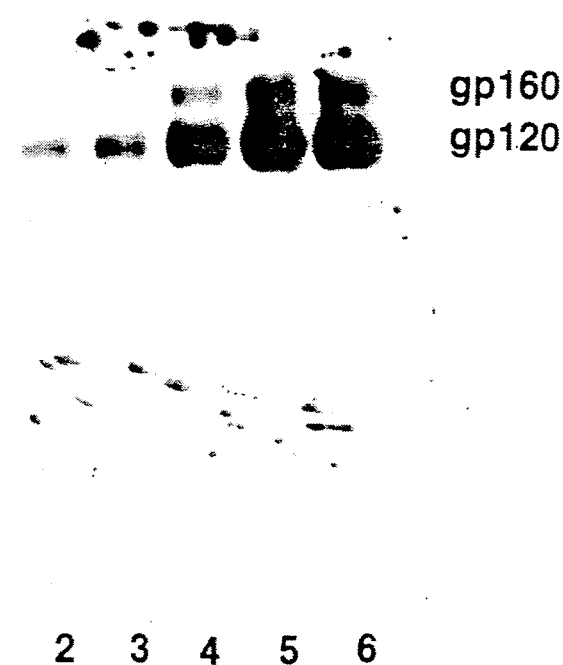
FIG. 4 shows the binding of gp120 and gp160 by CD4. Conditioned medium from a $^{35}$S-methionine labeled 6D5$_{451}$ culture was clarified by centrifugation at 2000× g followed by filtration through a 0.45 u filter. One-half milliliter of the medium was incubated with CEM$_{50}$ cells in a total volume of 2 ml, as described below. The bound proteins were immunoprecipitated with OKT4 antibody. Lane 1: 0.5×10$^6$ cells; Lane 2: 1×10$^6$ cells; Lane 3: 2×10$^6$ cells; Lane 4: 5×10$^6$ cells; Lane 5: 10×10$^6$ cells; Lane 6: 20×10$^6$ cells.

Although the primary target of HIV-1 infection is the helper/inducer subset of T lymphocytes bearing CD4 cell surface markers, the actual mechanism by which the virus infects susceptible target cells is only beginning to be understood. Monoclonal antibodies to certain epitopes of CD4 antigens were found to block viral infection and could immunoprecipitate complexes of CD4 and gp120. This tends to suggest that the key interaction between the gp120 and CD4 initiates the infection process of HIV-1. One consequence of the virus infection is the formation of multinucleated giant cells resulting from cell fusion events. A clone of CEM cells has been shown to exhibit rapid and quantitative syncytia formation when mixed with HIV-1-infected cell lines [Mathews, et al., *PNAS, USA* 84:5424-5428(1987)] (FIG. 3B). This type of syncytia formation often serves as a measure of gp120-CD4 interaction during virus infection. The ability of HTLV-III$_{451}$ glycoprotein to interfere with HTLV-III$_B$-induced fusion of CEM cells was assayed by incubation of the target CEM cells with a partially purified preparation of glycoprotein before mixing with Molt-3/HTLV-III$_B$ cells for 36 hours. Preincubation of CEM cells with glycoprotein preparations from uninfected 6D5 cells had no effect on the formation (FIG. 3C). In contrast, pretreatment of the syncytia formation (FIG. 3C). In contrast, pretreatment of the CEM cells with the HTLV-III451 glycoprotein preparations completely blocked the syncytia formation induced by HTLV-III$_B$/Molt-3 cells (FIG. 3D). This suggests that the viral glycoprotein could selectively bind with CD4 antigens on target cells, thereby blocking infection by the HIV-1 infected cells.

By immunoprecipitation with a human serum, more than 90% of the viral glycoproteins were found in the soluble form after high speed centrifugation of the conditioned medium. The interaction of HTLV-III$_{451}$ glycoprotein with the CD4 molecule was further examined by the specific binding of labeled gp120 and gp160 to CEM cells. For this purpose, cell-free supernatant form $^{35}$S-methionine labeled 6D5$_{451}$ was incubated with increasing numbers of CEM cells. After washing the cells with PBS, the bound HIV glycoprotein-CD4 complex on the cells was solubilized with detergents as described alone. The solubilized extract was immunoprecipitated with two monoclonal antibodies to the CD4 molecule. Both HIV glycoproteins were precipitated by OKT4. It is, however, interesting that when the receptor density was limiting, gp120 was the predominant species that was bound to the cells. At higher cell density, when binding sites were more abundant, both gp160 and gp120 were clearly evident in the CD4 complex. The CD4-glycoprotein complex could not be precipitated with the monoclonal OKT4A. This is consistent with the previous observations that the site of attachment of HIV gp120 on the CD4 molecule is the OKT4A epitope. The relative affinity of the receptor site appears to favor gp120 over gp160 based on the observation that virtually no gp160 was bound from a mixture of gp120 and gp160 at limiting CD4 concentrations. How much of this difficulty of binding is dictated by topological constraints on the larger gp160 in approaching the cell surface CD4 is yet to be determined.

While particular embodiments of the invention have been described, it will be understood, of course, that the invention is not limited thereto, and that many obvious modifications and variations thereof can be made, and that such modifications are intended to fall within the scope of the appended claims.

What is claimed is:

1. A method for the production of native human immunodeficiency virus gp160 comprising:
    infecting cells from a HUT78 T-cell line with HTLV-III$_{451}$;
    selecting infected HUT78 cells that produce native gp160;
    incubating said gp160 producing cell line in serum-free medium under conditions that promote cell growth; and
    isolating native gp160 from said medium.

2. In a process for the production of envelope proteins from human immunodeficiency virus wherein a T-cell line is infected with said virus, incubated in a medium under conditions that promote cell growth, and glycoproteins are secreted into said medium, the improvement which comprises:
    incubating cells from a gp160 producing 6D5$_{451}$ infected T-cell line in serum-free medium, and
    isolating from said medium a 160 kD protein which corresponds to native HIV envelope glycoprotein gp160.

* * * * *